(12) United States Patent
Jung et al.

(10) Patent No.: US 7,785,649 B2
(45) Date of Patent: Aug. 31, 2010

(54) METHOD FOR MANUFACTURING PROTEIN CHIP SUBSTRATE USING PLASMA AND PROTEIN CHIP SUBSTRATE MANUFACTURED BY THE METHOD

(75) Inventors: Dong-geun Jung, Gangnam-gu (KR);
Sang-hak Yeo, Gangbuk-gu (KR);
Chang-rok Choi, Gunpo-si (KR)

(73) Assignee: Sungkyunkwan University Foundation for Corporate Collaboration, Suwon-si (KR)

( * ) Notice: Subject to any disclaimer, the term of this patent is extended or adjusted under 35 U.S.C. 154(b) by 916 days.

(21) Appl. No.: 11/616,483

(22) Filed: Dec. 27, 2006

(65) Prior Publication Data

US 2007/0166815 A1 Jul. 19, 2007

(30) Foreign Application Priority Data

Dec. 28, 2005 (KR) .................. 10-2005-0131921

(51) Int. Cl.
*A61L 33/00* (2006.01)

(52) U.S. Cl. .............. 427/2.14; 427/2.11; 427/2.1; 427/457; 427/458; 427/487; 427/488; 427/491; 427/508; 427/509; 427/533; 427/535; 427/536

(58) Field of Classification Search .............. 427/2.14
See application file for complete search history.

(56) References Cited

FOREIGN PATENT DOCUMENTS

WO    WO02064654 A1 *  8/2002

\* cited by examiner

*Primary Examiner*—Michael Barr
*Assistant Examiner*—Andrew Bowman
(74) *Attorney, Agent, or Firm*—Oblon, Spivak, McClelland, Maier & Neustadt, L.L.P.

(57) ABSTRACT

Disclosed herein are a protein chip substrate and a method for manufacturing the protein chip substrate. The method includes deposition of plasma polymerized ethylenediamine (PPEDA) having an amine group on plasma polymerized cyclohexnane (PPCHex) by inductively coupled plasma-chemical vapor deposition (ICP-CVD), thereby preventing non-specific adsorption of proteins on a slide surface.

13 Claims, 9 Drawing Sheets

METHOD FOR MANUFACTURING PROTEIN CHIP SUBSTRATE USING PLASMA AND PROTEIN CHIP SUBSTRATE MANUFACTURED BY THE METHOD

BACKGROUND OF THE INVENTION

1. Field of the Invention

The present invention relates to a protein chip substrate and a method for manufacturing a protein chip substrate. More specifically, the present invention relates to a method for manufacturing a protein chip substrate wherein plasma polymerized ethylenediamine (PPEDA) having an amine group is deposited on plasma polymerized cyclohexane (PPCHex) being free of non-specific adsorption by inductively coupled plasma-chemical vapor deposition (ICP-CVD), thereby preventing non-specific adsorption of proteins on a slide surface, and a protein chip substrate manufactured by the method.

2. Description of the Related Art

With recent discoveries of human genomic structures, research for human genomic functions has increasingly attracted considerable attention.

There have been advances in a new research field referred to as "functional proteomics" for systematically probing functions of human genes.

Functional proteomics is divided into three groups of "genomics", "proteomics" and "bioinformatics". Genomics is focused on studies targeting genes, proteomics is focused on studying the behavior of genes by targeting overall proteins in cells, and bioinformatics is a combined-approach of the two fields.

Molecular biological access to function studies for genes or cells was made on the basis of controlling a single gene or mRNA expressed by the gene. Nowadays, the recent trend towards proteome-based analysis is being introduced.

Protein chips are required for the proteome-based analysis as a key technique (Gavin MacBeath and Stuart L. Schreiber, Science, 289:1760~1763, 2000).

The protein chips are an automatic system capable of simultaneously analyzing binding structure of a large amount of proteins by immobilization of tens to thousands of proteins on a small substrate.

The protein chips are similar to microarray DNA chips which detect gene expressions or mutants by immobilizing tens to thousands of genes on a small substrate, and simultaneously analyzing variations in a large amount of genes through the behavior of complementary bindings between genes (Yasuda, H., Lamage, C. E., J. A ppl. Polym. Sci. 17: 201, 1973; Muguruma, H., Karube, I., Trends Anal. Chem. 18: 62, 1999; Nalanishi, K., Muguruma, H., Karube, I., Anal. Chem. 68: 1695, 1996; Miyachi, H., Hiratsuka, A., Ikebukuro, K., Yano, K., Muguruma, H., Karube, I., Biotechnol. Bioengin. 69: 323, 2000).

However, protein chips can be used for the following analysis unattainable by DNA chips.

First, they can be used to obtain information regarding interaction between protein-protein. The signal transmission or control within cells is represented as the interaction between protein-protein. Thus, this can be analyzed by protein chips.

Second, proteins, from higher organisms including humans to yeasts, undergo post-translational modification. As a result, it is possible to obtain information regarding a secondary modification such as phosphorylation and oxidation.

Third, proteins enable detection of problems which may be generated after mRNA formation. A variety of diseases are caused by problems associated with post-transcription control, protein generation and protein localization. DNA chips used to detect mRNAs make it difficult to obtain information regarding the problems.

Fourth, when proteins are expressed from mRNAs, correlation in quantity between the proteins and mRNAs is often not sufficiently high. Thus, in some cases, DNA chips have limitation of difficulty in obtaining correct information associated with proteins. However, protein chips enable solving such limitation of DNA chips.

Fifth, difference in base sequence of genes revealed by DNA chips is not directly indicative of disease or difference in phenotype. Furthermore, since mutants derived from amino acids having similar characteristics generally retain inherent characteristics of proteins, they hardly cause disease or difference in phenotype.

On the other hand, the use of protein chips enables identification of the protein inducing disease or difference in phenotype.

In addition, the use of protein chips ensures database formation for relationship between protein-protein, and is effective in reducing time and costs upon development of novel medicines. For example, a period required to develop a treatment medicine using protein chips can be considerably shortened, as compared to the cases using current genes.

Protein chips are utilized in a wide variety of industrial applications including disease diagnosis, environment monitoring and harmfulness testing, as well as industrial applications.

Based on the mentioned advantages, protein chips are expected to have high marketability, as compared to DNA chips. Thus, there is an eager demand for developing protein chips.

Such a protein chip includes a sensor chip and a protein detection system.

The sensor chip is a major constituent for determining a developing rate of the protein chip.

The sensor chip has a structure in which tens to thousands of proteins are arranged in a predetermined array on the surface of a small chip. The chip is selected from a slide-sized glass or plastic.

A key technique associated with the sensor chip is protein immobilization for attaching proteins to the surface thereof.

The protein immobilization techniques are classified into three groups, based on the characteristics.

First, immobilization of a specific protein to the surface of sensor chips using carboxymethyl-dextran (CM) is the most widely used method. Here, amine coupling is the most commonly used. Alternately, thiol coupling or avidin-biotin coupling is used to immobilize acid proteins or DNAs.

Second, surface treatment of sensor chips is suitable for immobilizing a plurality of protein groups having the same characteristics.

Third, poly lysine or calyx crown is available for immobilizing large amount of non-specific proteins.

The control of protein immobilization and patterned array of biomolecules are implicated in wide a variety of fields including basic studies of biochips, bioelectronics and cell-biology.

A variety of techniques, e.g., self-assembled monolayer and lithography, are generally used for protein immobilization.

In recent years, studies for immobilizing bio molecules on a solid slide using plasma polymerized films have been actively investigated.

Plasma is a state in which neutral gas molecules absorb electrical or thermal energy, and are then separated into ions and electrons.

Studies associated with techniques utilizing plasma have been actively made.

Plasma is being gradually expanded to a variety of applications including plasma etching and plasma enhanced chemical vapor deposition (PECVD) in semiconductor device fabrication, surface treatment of metals or polymers, synthesis of enhanced materials (e.g., imitation diamonds), plasma display panels (PDPs) and environment protection techniques.

Plasma partially ionizes gas, and efficiently activates molecules.

Relatively inert molecules are exposed to plasma, thereby being readily activated.

Coating of plasma polymerized films is achieved by arranging monomers in a deposition chamber, activating or decomposing reactants with plasma, and allowing the reactants to be condensed on the surface of a slide, to form a polymerized film.

When precursors containing an amine or aldehyde group are used, plasma polymerized films can contain a large amount of the group. Thus, such solid slide is utilized in biomolecules immobilization.

The plasma polymerized films are largely different with chemically-polymerized general films.

Such plasma polymerized film has no porosity, is mechanically and chemically stable, and has an adhesive property to the slide due to its cross-linked structure.

In addition, the plasma polymerized film has superior controllability in thickness and high uniformity, as compared to chemically-polymerized films. These advantages provide suitability for manufacture of protein and DNA arrays.

To achieve highly sensitive diagnostic protein chips, a sufficient amount of proteins must be immobilized at a predetermined space thereof. Accordingly, there is a demand for methods that can immobilize proteins more efficiently.

Protein immobilization based on covalent bonds depends on nucleophilicity or electrophilicity due to chemical or physical formation on the surface of the slide glass.

A well-known problem in experiments associated with protein chips is non-specific adsorption of proteins on the surface of the slide glass. The non-specific adsorption is misrecognized as obviously false response in diagnostic inspection.

However, conventional protein chips have a problem of occurrence of non-specific adsorption even in a region where no amine group exists.

Thus, there is a need for techniques that minimize non-specific adsorption upon diagnosis based on protein chips.

SUMMARY OF THE INVENTION

It is an object of the present invention to prevent non-specific adsorption of proteins on a slide surface in protein immobilization.

To accomplish the above-mentioned object, the present invention suggests that plasma polymerized ethylenediamine (hereinafter, referred to simply as "PPEDA") having an amine group is deposited on plasma polymerized cyclohexnane (hereinafter, referred to simply as "PPCHex") being free of non-specific adsorption by inductively coupled plasma-chemical vapor deposition (ICP-CVD).

Ethylenediamine and cyclohexanane are used as precursors for the PPEDA and PPCHex, respectively.

Detailed modification of chemical properties of a slide glass is required for protein immobilization.

The PPCHex was deposited on the slide glass. As a result, the surface of the slide glass becomes hydrophilic.

The PPEDA was patterned on the resulting structure (PPCHex/glass slide) using a patterned mask.

The hydrophilicity or hydrophobicity of each film is determined by measuring the contact angle between water and the film.

The contact angle between water and the surface of PPEDA film was about 45°. This indicates that the PPEDA film surface is hydrophilic.

On the other hand, the contact angle between water and the surface of PPCHex film was equal to or greater than 90°. This indicates that the PPCHex film surface is hydrophobic.

The PPEDA film deposited under suitable conditions hardly had non-specific binding.

The PPCHex film being free of non-specific adsorption was evaluated for roughness and chemical structure with an atomic force microscopy (APM) and Fourier transform infrared spectroscopy, respectively.

Immobilized proteins and the degree of non-specific adsorption are measured by fluorescence detection with an exciting wavelength of 490 nm and an emitting wavelength of 520 nm.

The immobilized proteins according to the present invention are observed only on the hydrophilic PPEDA patterned on PPCHex film being free of non-specific adsorption.

As a result, the inventors found that proteins tend to be immobilized on the PPEDA being hydrophilic and having an amine group, exclusively.

The method of the present invention enables proteins to be immobilized in a desired region and proteins to be arranged in a predetermined position, thus being very valuable.

Accordingly, patterning techniques of plasma polymerized cyclohexnane (PPCHex) being free of non-specific adsorption on plasma polymerized ethylenediamine (PPEDA) having an amine group suggests an advanced technical trend in biochip analysis.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Detailed description will be made of preferred embodiments of the present invention with reference to the accompanying drawings. However, various changes and modifications may be made to the preferred embodiments of the invention and the invention is not to be construed as being limited to the embodiments.

According to a method for manufacturing a protein chip of the present invention, attaching precursor molecules to a substrate is preferably carried out by inductively coupled plasma-chemical vapor deposition (ICP-CVD).

Figure 1:
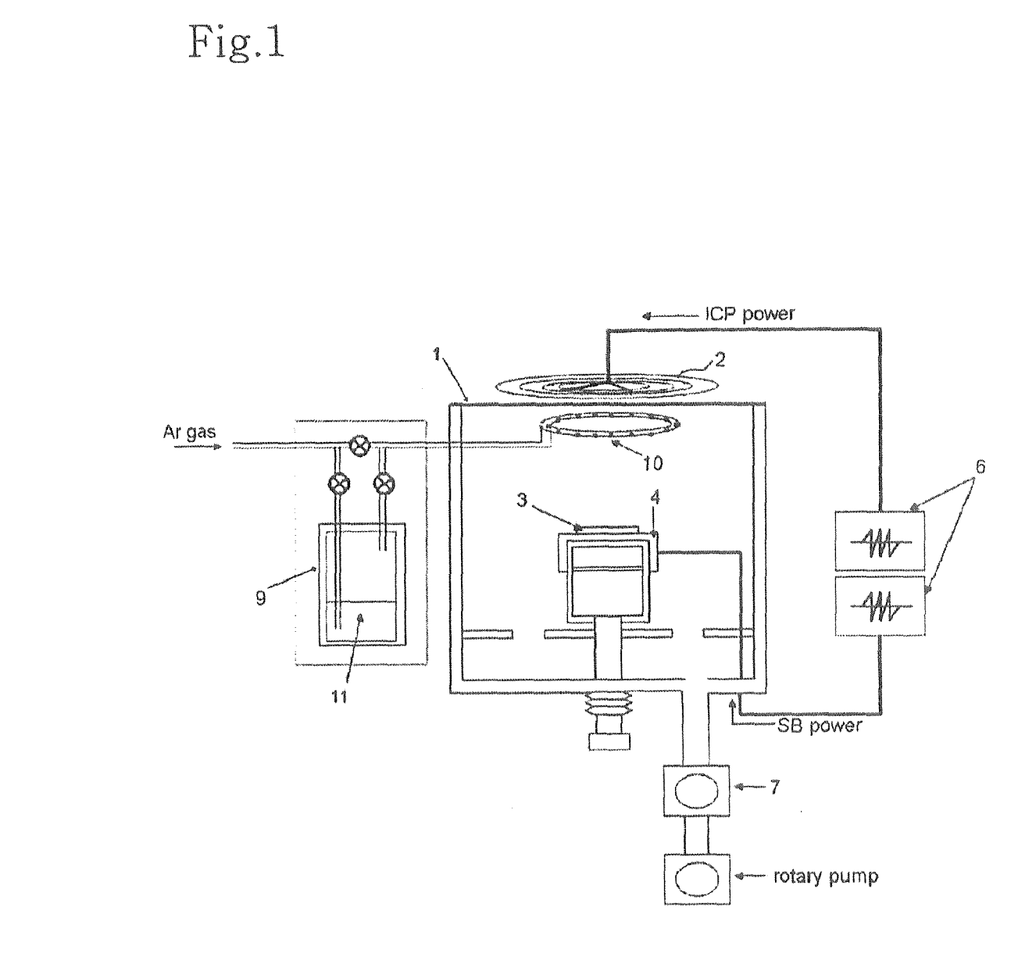
FIG. 1 is a diagram schematically illustrating an inductively coupled plasma-chemical vapor deposition (ICP-CVD) system used in manufacture of a protein chip substrate according to the present invention.

FIG. 1 is a diagram schematically illustrating an ICP-CVD system used in manufacture of a protein chip substrate according to the present invention.

The ICP-CVD system includes a plasma reaction chamber 1, a vacuum device 7 to control a pressure inside the plasma reaction chamber 1, a bubbler 9 to allow a precursor 11 in the form of gas to be fed into the plasma reaction chamber 1, a shower ring 10 to spray the vaporized precursor from the bubbler 9 to the plasma reaction chamber 1, an outer electrode 2 arranged on the plasma reaction chamber 1, a substrate supporter 4 to support a substrate 3 and function as an inner electrode, the substrate supporter 4 arranged inside the plasma reaction chamber 1, a radio frequency generator (RF generator) 6 to supply inductively coupled plasma (ICP) power to the outer electrode 2 and supply slide voltage (SB) power to the substrate supporter 4.

The ICP-CVD system further includes a gas repository to store a carrier gas such as He and Ar (not shown), a flow regulator to control moles of passing gas (not shown), a cooler to control a temperature inside the chamber (not shown) and a fan to promote convection inside the chamber (not shown).

The substrate supporter 4 is provided with a heater therein.

A method for depositing a thin film using the ICP-CVD system to manufacture a protein chip substrate according to the present invention will be described as follows.

First, a plasma-polymerized cyclohexane (PPCHex) film using cyclohexane (CHex) as a precursor was deposited on a slide glass as a substrate by ICP-CVD.

Next, a plasma-polymerized ethylenediamine (PPEDA) film using ethylenediamine (EDA) as a precursor was deposited on the PPCHex film by ICP-CVD.

A method for depositing the PPCHex film on the substrate will be described as follows.

The substrate 3 was sequentially washed with trichloroethylene, acetone and methanol, and was then arranged on the substrate supporter 4 inside the plasma reaction chamber 1.

Next, the pressure inside the chamber 1 was controlled by the vacuum device 7. Cyclohexane as a precursor together with the carrier gas was fed into the chamber 1 by the bubbler 9. The temperature inside the chamber 1 was elevated by the heater under the substrate supporter 4.

When inductively coupled plasma (ICP) power and slide voltage (SB) power are applied to the outer electrode 2 and the substrate supporter 4 by the RF generator 6, respectively, plasma generated by the outer electrode 2 and the substrate supporter 4 (inner electrode) was formed between the substrate 3 and the chamber 1.

At this time, cyclohexane was polymerized by the plasma, the plasma polymerized cyclohexane (PPCHex) film was uniformly deposited on the substrate 3.

The deposition chamber used in the present invention has a structure of cylinder and is made of a stainless material. The chamber has a diameter of 30 cm and a height of 28 cm.

Cyclohexane monomer was put in the bubbler 9 adjusted to a temperature of 50° C.

Cyclohexane was vaporized by using Ar as inert carrier gas, and was then fed into the chamber 1.

In addition, SB power generates plasma around the slide owing to a high-frequency generator arranged on the substrate supporter 4.

The walls of the deposition chamber 1 were grounded.

The deposition chamber 1 was maintained at a base pressure of approximately $10^{-5}$ Torr, by vacuum device 7.

The PPEDA film was maintained at a temperature of 27° C.

The precursors were preferably fed into the chamber 1 by using a carrier gas. The examples of the carrier gas include Ar, $N_2$, He and $H_2$. More preferred is Ar.

The PPEDA film was deposited on the slide glass used as the substrate 3, while maintaining Ar flow ratio of about 20 sccm.

The deposition was carried out under a pressure of 300 mtorr for 30 sec.

The ICP power applied from the RF generator 6 to the outer electrode was preferably maintained at 15 W.

The SB power applied from the RF generator 6 to the substrate supporter 4 as an inner electrode was elevated from 10 W to 70 W.

Subsequently, a plasma-polymerized ethylenediamine (PPEDA) film using ethylenediamine (EDA) as a precursor by ICP-CVD was deposited on the PPCHex film through a patterned mask, thereby patterning the PPEDA film.

At this time, the deposition was conducted at room temperature and an Ar flow of about 30 sccm. The deposition was conducted at a pressure of 30 mtorr for about 2 min. The ICP and SB powers were maintained at 4 W and 3 W, respectively.

1-Ethyl-3-[3-dimethylaminopropyl]carbodiimide hydrochloride (EDC) and fluorescein isothiocyanate (FITC)-conjugated Goat anti-Rabbit immunoglobulin G (IgG) were used in Examples of the present invention. In addition, a diluted solution of each reagent in phosphate buffered saline (PBS) was used in Examples.

As plasma deposition system used in Examples of the present invention, any outer electrode and substrate supporter may be used without any particular limitation in terms of material and structure so long as they are commonly used in chemical vapor deposition systems.

In particular, the outer electrode is preferably formed of a flat circular coil. The outer electrode is preferably made of material being chemically stable and being in little danger of contamination. The more preferred material is a stainless material.

The substrate is preferably made of one selected from the group consisting of glass, plastic, metal and silicone. Preferred is glass.

Efficiency of protein immobilization in films manufactured according to the present invention was evaluated by measuring contact angle, fluorescence, surface roughness by atomic force microscope (AFM), and chemical structure by Fourier transform infrared spectroscopy (FTIR) The evaluation will be described in detail as follows.

Contact Angle Measurement

The present inventors measured the static contact angle between water of 2 µl and samples. The measurement was based on the digital image recoded with a charge-coupled device (CCD) as equal to the level of the sample.

The static contact angle measurement enables evaluation of the degree of hydrophilicity or hydrophobicity.

Figure 2:
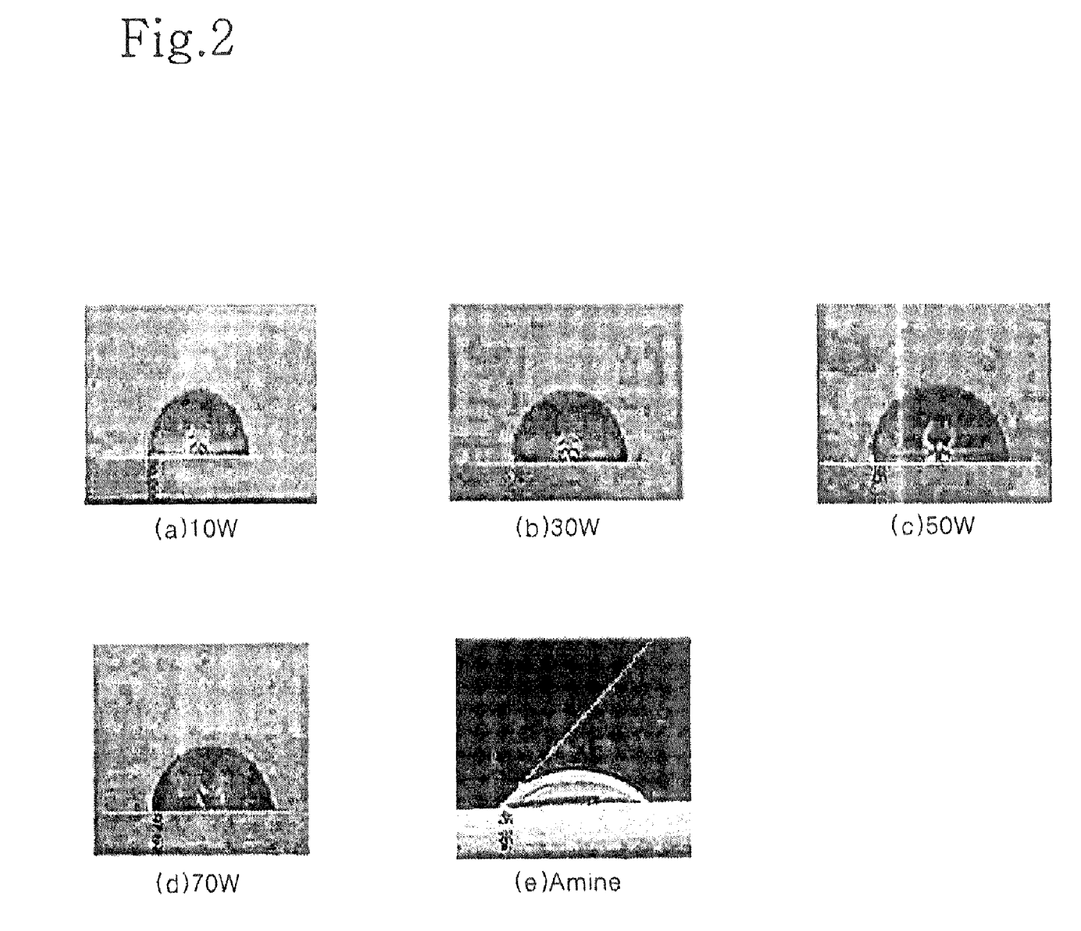
FIG. 2 are photographs illustrating the static contact angle between water and each film measured by a charge-coupled device (CCD), respectively.
Figure 3:
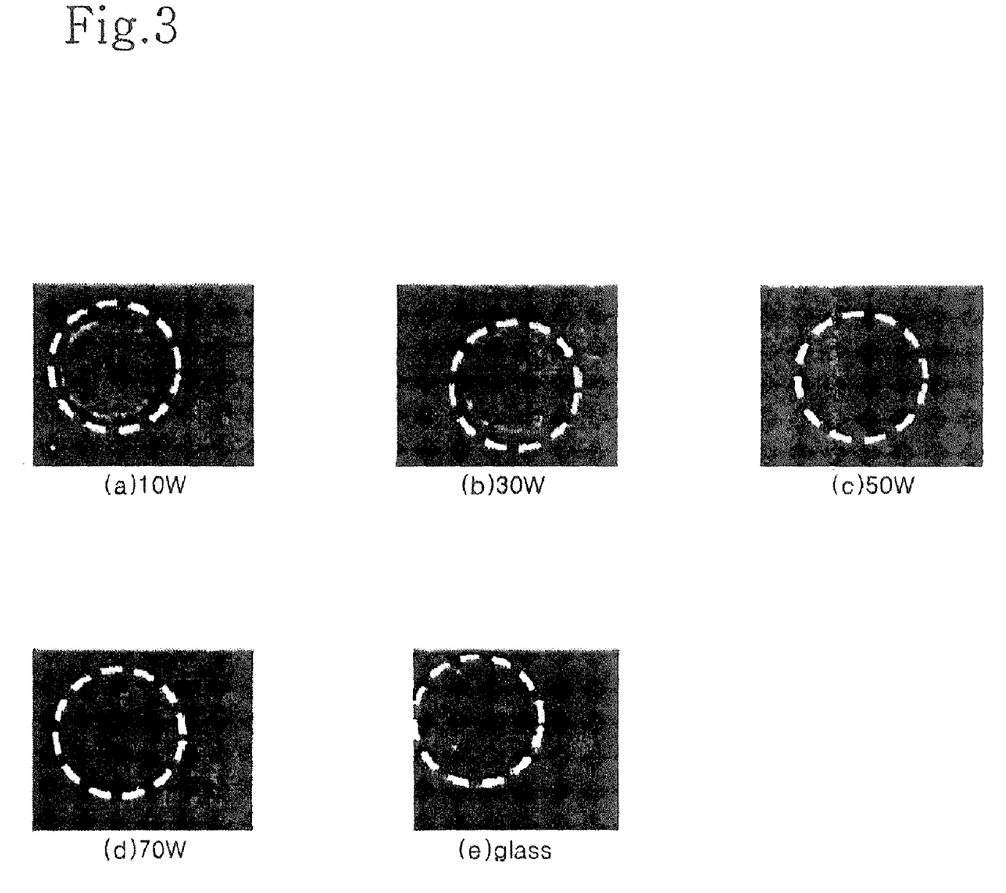
FIG. 3 are photographs illustrating non-specific protein immobilization on each PPCHex slide glass.

The results are shown in FIG. 2.

The contact angle between water and the surface of PPEDA film was about 45°. This indicates that the PPEDA film surface is hydrophilic (FIG. 2F).

An amine group is reported to have hydrophilicity and a superior protein-binding capability.

On the other hand, the contact angle between water and the surface of PPCHex film was equal to or greater than 90°. This indicates that the PPCHex film surface is hydrophobic (FIGS. 2A to 2E).

Hydrophobic surfaces mean that a weak interaction exists between water and the film. The film surfaces have a hydrocarbon group (—CHx) only.

Meanwhile, hydrophilic surfaces mean that a strong interaction exists between water and the film. The film surfaces have an oxygen group.

Protein Immobilization

Patterned slide glasses were cultured in 1-Ethyl-3-[3-dimethylaminopropyl]carbodiimide hydrochloride (EDC) solution at room temperature for 10 min. Then, the slide glasses were washed with deionized water.

4 ng/uL of fluorescein isothiocyanate (FITC)-conjugated Goat anti-Rabbit immunoglobulin G (IgG) solution was cultured on the slide glasses for 1 hour.

The resulting IgG culture was washed with deionized water, followed by drying.

Fluorescence Measurement

The resulting protein-immobilized FITC-conjugated IgG was scanned with a laser fluorescent scanner.

The protein-immobilized FITC-conjugated IgG was excited at 490 nm and emitted at about 520 nm.

Non-specific protein adsorption on each of the PPCHex slide glasses was analyzed for fluorescence measurement.

The PPCHex slide glasses deposited at different powers were prepared. Each of the PPCHex slide glasses was evaluated for suitability for use in protein chips.

FIGS. 3A to 3E are CCD fluorometric images confirming non-specific protein immobilization on the PPCHex slide glasses, respectively.

As can be seen from FIGS. 3A to 3E, as SB power is elevated from 10 W to 70 W, non-specific protein adsorption decreases.

In particular, non-specific protein adsorption was not shown at a plasma SB power of 70 W.

Figure 4A:
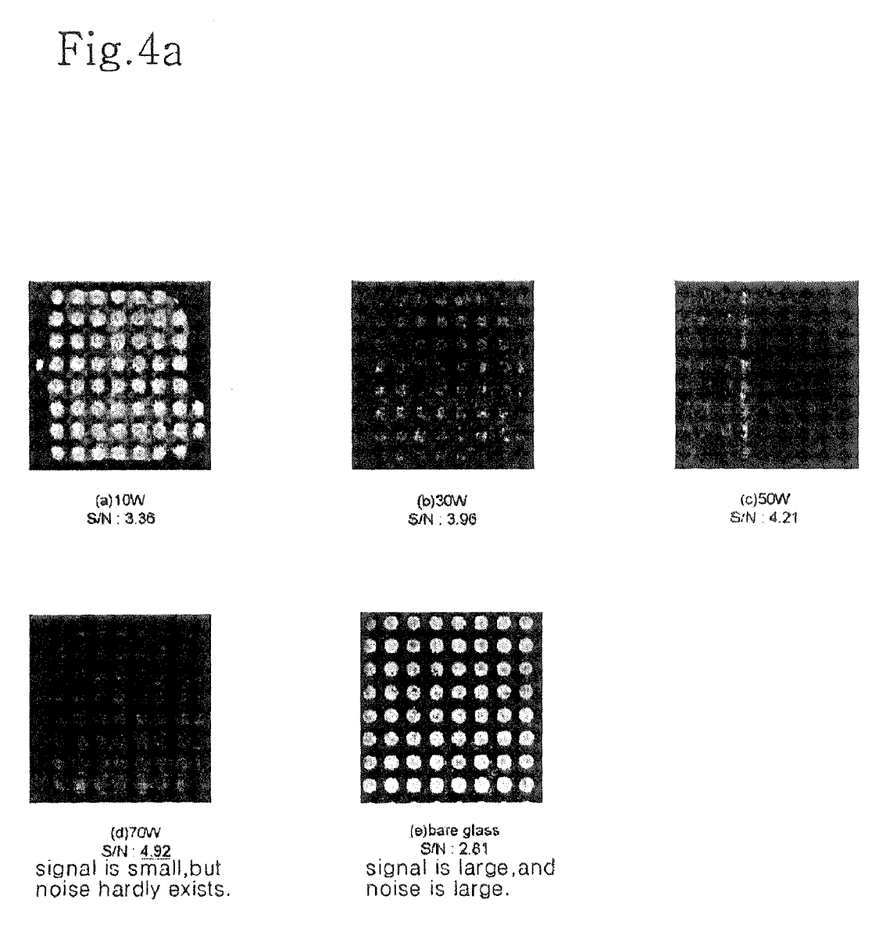
FIG. 4A are photographs illustrating an average signal-to-noise ratio and fluorescence intensity of each PPEDA slide glass before imaging.
Figure 4B:
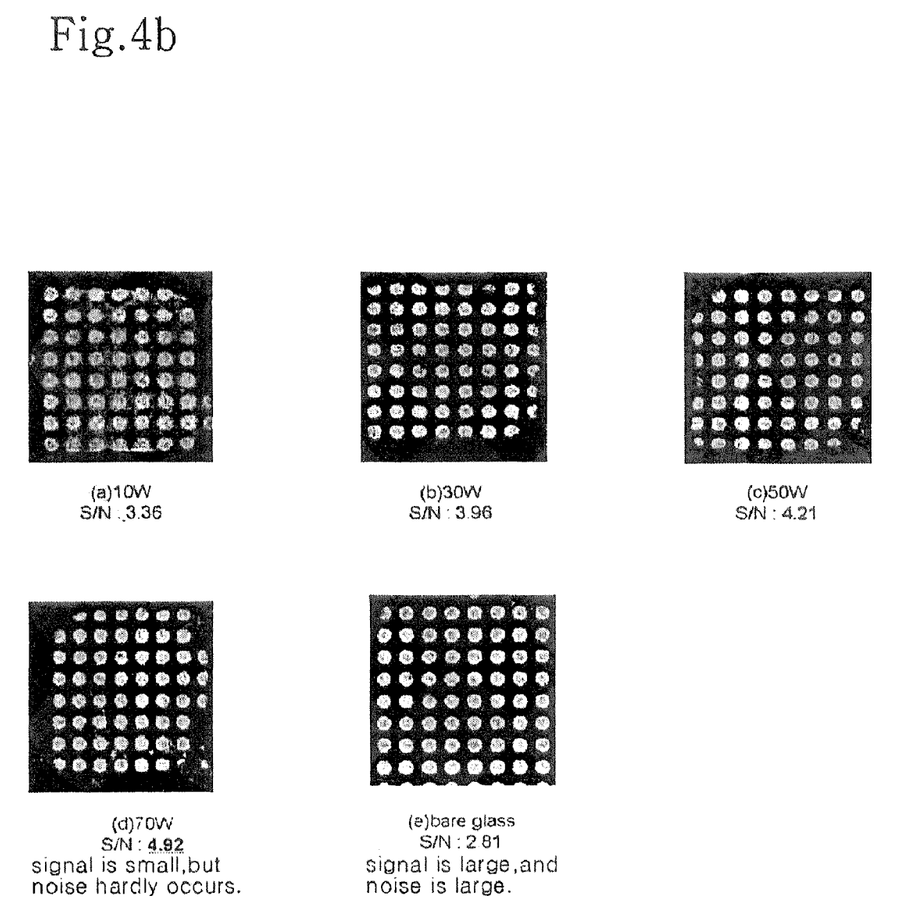
FIG. 4B are photographs illustrating an average signal-to-noise ratio and fluorescence intensity of each PPEDA slide glass after imaging.
Figure 4C:
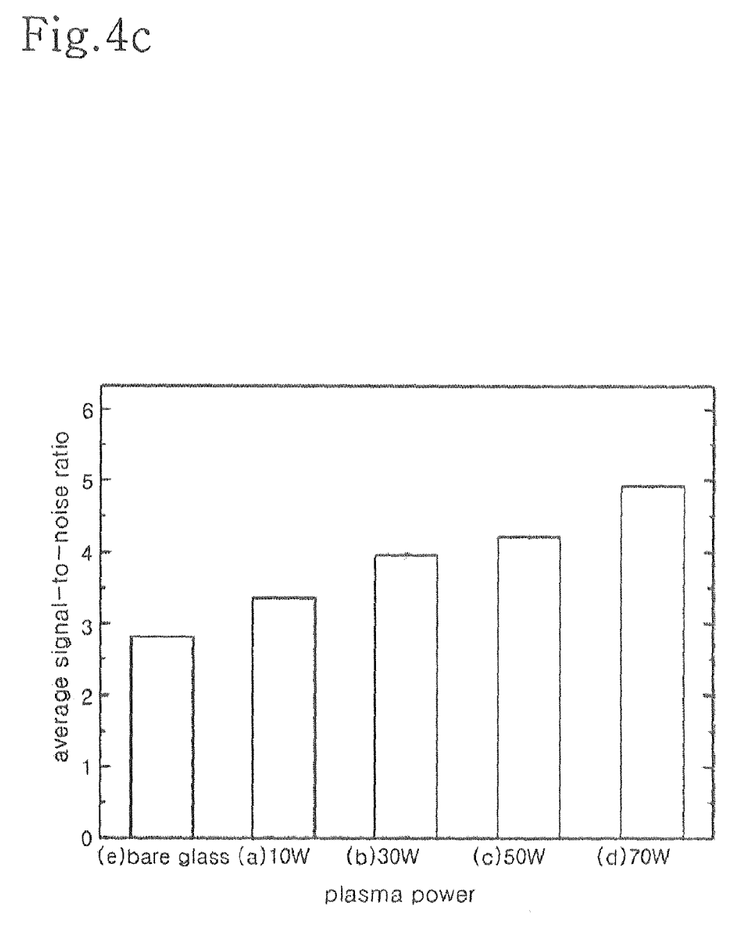
FIG. 4C is a graph illustrating changes in average signal-to-noise ratio of a PPEDA slide glass as an increasing function of plasma power.

FIGS. 4A to 4C show an average signal-to-noise ratio and fluorescence intensity of PPEDA slide glasses deposited on PPCHex films and a PPEDA slide glass, respectively.

FIG. 4A shows an average signal-to-noise ratio and fluorescence intensity of a PPEDA slide glass before imaging.

FIG. 4B shows an average signal-to-noise ratio and fluorescence intensity of a PPEDA slide glass after imaging.

FIG. 4C is a graph showing comparison of changes in average signal-to-noise ratio of a PPEDA slide glass as an increasing function of plasma power.

In FIG. 4A, (a) shows an average signal-to-noise ratio of a PPEDA slide glass deposited on a PPCHex film at a plasma SB power of 10 W. (b) shows an average signal-to-noise ratio of a PPEDA slide glass deposited on a PPCHex film at a plasma SB power of 30 W. (c) shows an average signal-to-noise ratio of a PPEDA slide glass deposited on a PPCHex film at a plasma SB power of 50 W. (d) shows an average signal-to-noise ratio of a PPEDA slide glass deposited on a PPCHex film at a plasma SB power of 70 W. (e) shows an average signal-to-noise ratio of a PPEDA slide glass deposited on a bare glass substrate.

As a result, the inventors have confirmed that SB deposition power has a great influence on the reduction in non-specific protein adsorption.

As can be seen from FIGS. 4A to 4C, the average signal-to-noise ratios for respective samples in accordance with variant deposition power were 3.36, 3.96, 4.21 and 4.92. Meanwhile, the average signal-to-noise ratio of the PPEDA slide glass deposited on the bare glass substrate without any PPCHex film was 2.81.

In the PPEDA slide glass deposited on the bare glass substrate without any PPCHex film, noise is increased, as signal is increased. On the other hand, in the PPEDA/PPCHex film deposited at a plasma SB power of 70 W, signal is small and noise hardly occurs.

Chemical Structure and Composition Analysis by FTIR

To find the cause of non-spesific adsorption, chemical structure and composition of the films were evaluated by Fourier transform infrared spectroscopy (FTIR).

FTIR spectra are normalized to the same peak value.

Figure 5A:
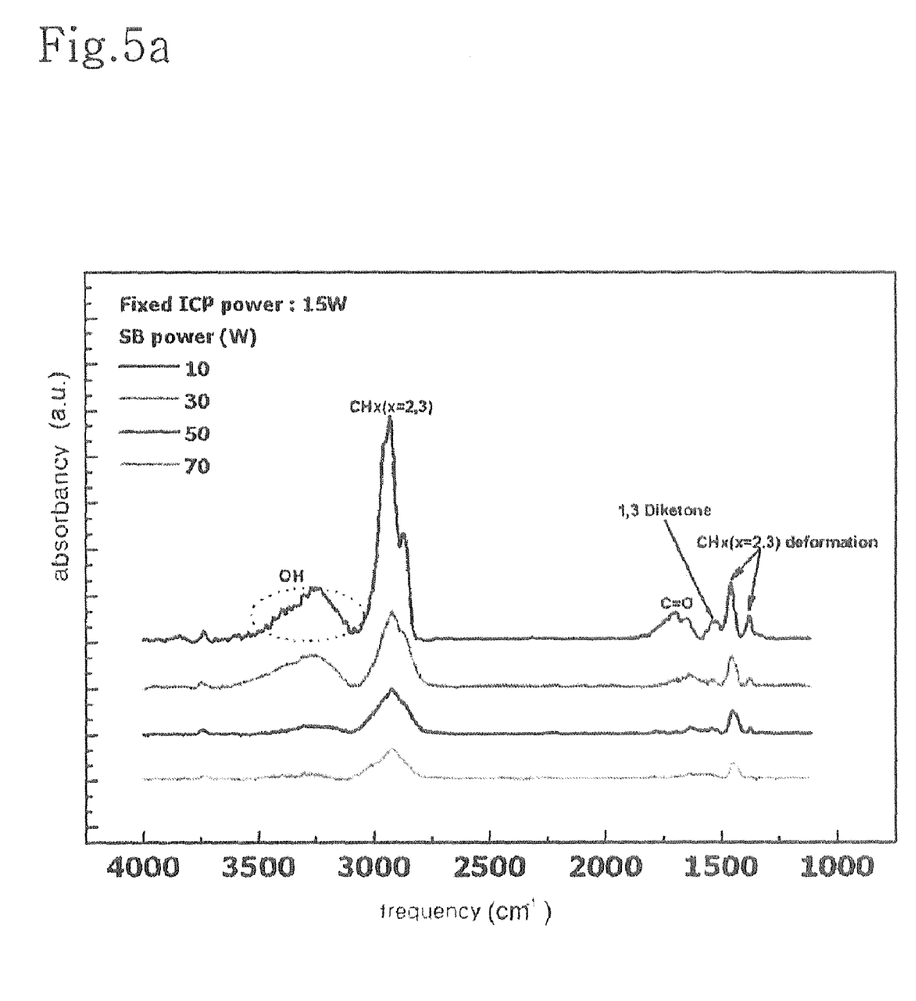
FIG. 5A is a graph illustrating a FTIR spectrum of a PPCHex film.

FIG. 5A shows a FTIR spectrum of the PPCHex film.

Figure 5B:
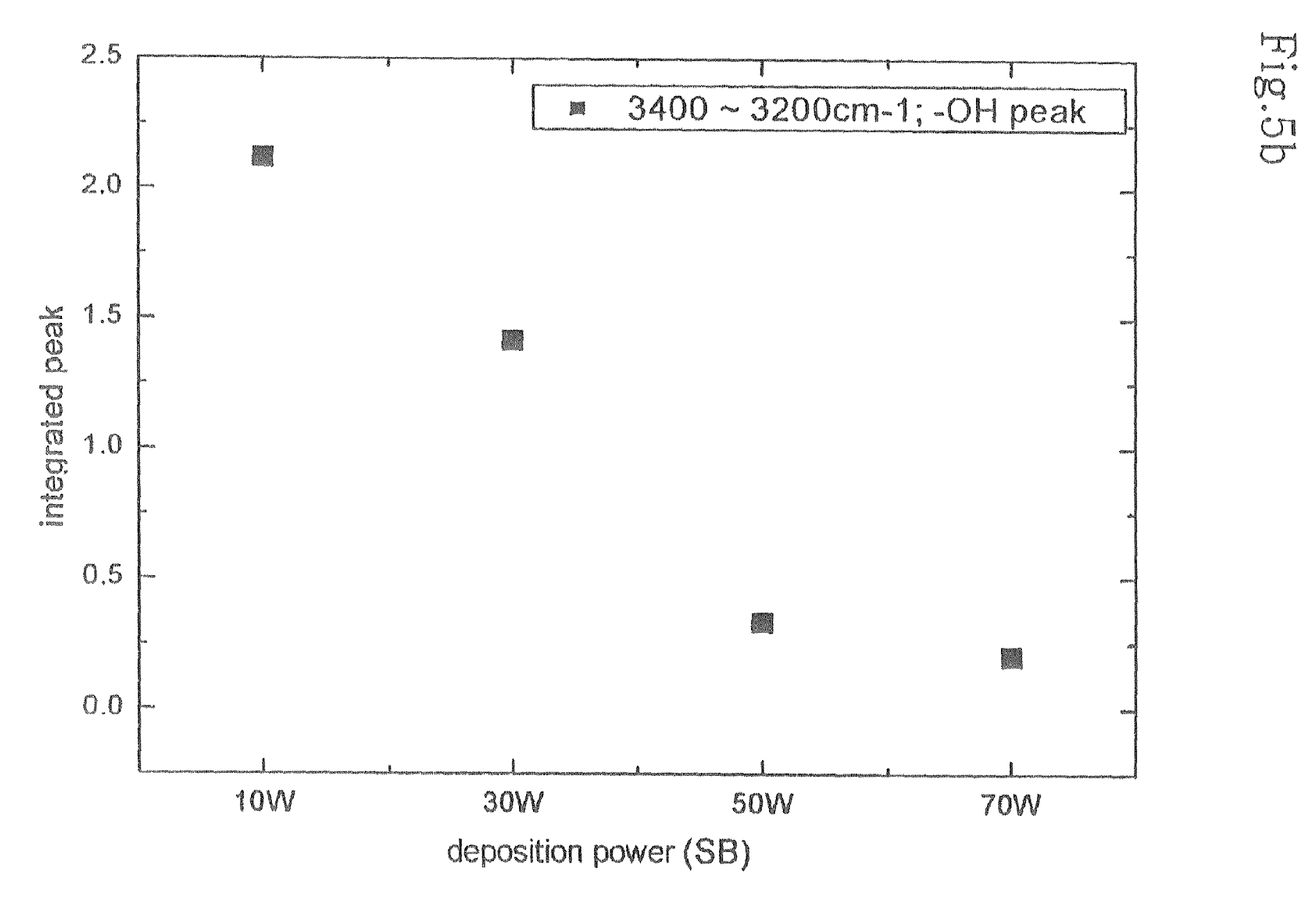
FIG. 5B is a graph illustrating changes in peak of a hydroxyl group (—OH) as a function of deposition power.

FIG. 5B is a graph illustrating changes in peak of a hydroxyl group (—OH) as a function of deposition power.

As shown in FIG. 5A, at SB powers of 10 W and 30 W, broad signals appear at frequencies of 3400 $cm^{-1}$ and 1650 $cm^{-1}$. This is the reason that moisture in air was adsorbed on the surface of PPCHex film deposited at 10 W and 30 W.

High signal peaks at 3400 $cm^{-1}$ and 1650 $cm^{-1}$ indicate that the PPCHex film surface has a hydroxyl group (—OH) which is generated from oxidation therein.

When a low plasma SB power of 10 W to 30 W is applied, cyclohexane precursors are incompletely decomposed, and are adsorbed in the form of a monomer.

At this time, the film is not densely packed. Accordingly, the film is exposed to air at room temperature, moisture is adsorbed on the surface thereof.

On the other hand, when a high plasma SB power of 50 W to 70 W is applied, cyclohexane precursors are completely decomposed, and are adsorbed in the form of a diamond-carbon.

In the FTIR spectrum, there is no signal peak at 3400 $cm^{-1}$ and 1650 $cm^{-1}$. But, peak of hydrocarbon group (—CHx, x=2 or 3) signal only appeared.

The PPCHex films deposited at different powers are compared. As a result, it could be confirmed that the PPCHex films were greatly different in chemical structure. This indicates that the film structure depends on the deposition power.

There has been reported that a hydroxyl (—OH) or aldehyde (—CHO) group present on the surface of glass induces chemical protein adsorption.

However, as shown in FIG. 5B, a peak for hydroxyl (—OH) or aldehyde (—CHO) hardly appears in the PPCHex film deposited at 70 W.

Relative area ratio of hydroxyl (—OH) peaks was decreased as a plasma power was increased.

It has been already reported that the difference in structure between the films considerably depends on the replacement of hydrophobic methyl (—$CH_3$) by hydrophilic hydroxyl (—OH).

Existence of such hydroxyl is indicative of formation of aldehyde, carbonyl and carboxyl, and thus occurrence of non-specific adsorption.

The overall PPCHex film exhibited considerably greater hydrophobicity. The PPCHex film deposited at 70 W has no adsorption of moisture or oxygen therein owing to its high denseness.

Surface Roughness Measurement by AFM

The slide glass was evaluated for surface roughness with an atomic force microscopy (AFM).

The AFM measurement was conducted in a contact mode and a measurement range of 1 µm.

Figure 6:
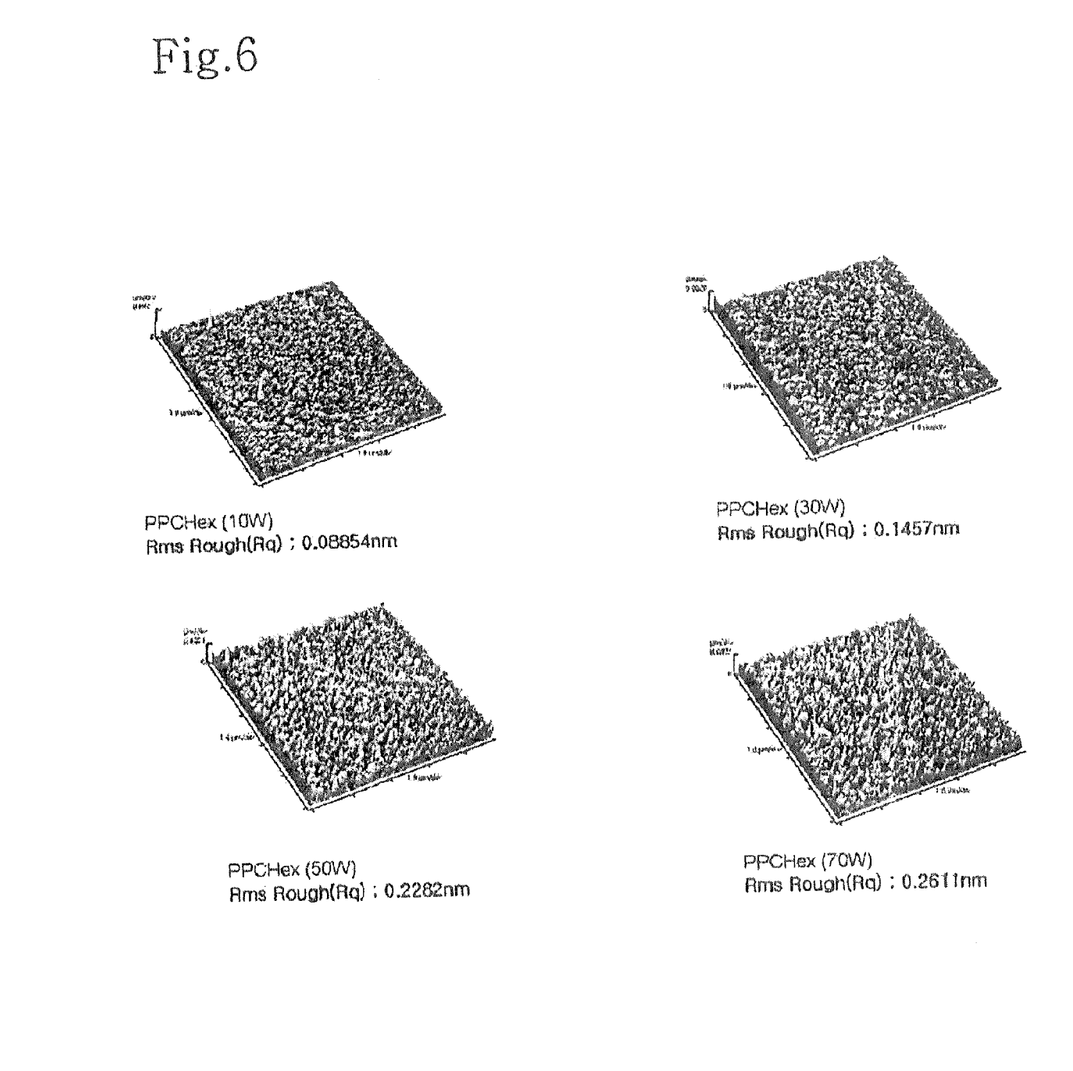
FIG. 6 are photographs illustrating a surface roughness of each PPCHex film.

FIG. 6 is a photograph illustrating a surface roughness of the PPCHex film.

As shown in FIG. 6, root mean square (RMS) values of surface roughness for samples at respective deposition powers were approximately 0.08854 nm, 0.1457 nm, 0.2282 nm and 0.2611 nm.

The PPCHex film deposited at a high power was rougher than the PPCHex films deposited at a low power. This is the reason that the surface of films is exposed to plasma upon deposition of PPCHex films. As a result, ionic or charged groups generated within the films by plasma at increased plasma power damaged the film surfaces.

The damage caused by such plasma is increased by elevating a plasma exposure power (i.e., deposition power). As a result, the PPCHex film surface was roughened.

It has already been reported in some cases that proteins tend to be readily adsorbed on a relatively rough surface.

From the results, it could be estimated that root mean square (RMS) values of the roughness were varied, but no physical protein adsorption occurred.

This estimation is based on the fact that the PPCHex film deposited at 70 W does not undergo considerable protein adsorption, although it has the highest roughness.

Accordingly, protein adsorption is caused by chemical adsorption, rather than physical adsorption.

As apparent from the above description, according to the method of the present invention, plasma polymerized ethylenediamine (PPEDA) having an amine group is deposited on plasma polymerized cyclohexnane (PPCHex) being free of non-specific adsorption by inductively coupled plasma-chemical vapor deposition (ICP-CVD).

Ethylenediamine and cyclohexnane are used as precursors for the PPEDA and PPCHex, respectively.

The PPEDA patterned on the PPCHex was subjected to protein immobilization.

The overall protein was immobilized on the hydrophilic PPEDA, rather than the PPCHex.

The PPEDA/PPCHex film exhibits improvement in signal-to-ratio value, as compared to the PPEDA film merely patterned without depositing any PPCHex.

The surface of the PPEDA/PPCHex film undergoes changes in chemical structure. The surface roughness is slightly increased from 0.08854 nm to 0.2611 nm, as deposition power is elevated from 10 W to 70 W.

As can be seen from the results, protein adsorption on the PPCHex film is caused by chemical adsorption, rather than physical adsorption.

Non-specific adsorption of proteins on the slide surface is a well-known problem in experiments associated with protein chips.

The inventors have solved the problem by introducing inductively coupled plasma-chemical vapor deposition (ICP-CVD).

It can be seen confirmed from the results that the ICP-CVD is practically applicable to protein microarray chips.

The method of the present invention prevents non-specific adsorption of proteins on the slide surface, thereby ensuring improvement in reliability of gene diagnosis techniques.

In addition, the method enables quick and uniform deposition of films on large-area substrates, thus realizing mass-production and commercialization.

Although the present invention has been described herein in detail with reference to its preferred embodiments, those skilled in the art will appreciate that these embodiments do not serve to limit the invention and that various changes and modifications may be made thereto without departing from the spirit and scope of the invention as defined in the appended claims.

What is claimed is:

1. A method for manufacturing protein chip substrate wherein plasma polymerized ethylenediamine (PPEDA) having an amine group is deposited on plasma polymerized cyclohexane (PPCHex) by inductively coupled plasma-chemical vapor deposition (ICP-CVD).

2. The method according to claim 1, the method comprising the steps of:
   (a) depositing a plasma-polymerized cyclohexane (PPCHex) film using cyclohexane as a precursor on a slide glass as a substrate by inductively coupled plasma-chemical vapor deposition (ICP-CVD); and
   (b) depositing a plasma-polymerized ethylenediamine (PPEDA) film using ethylenediamine (EDA) as a precursor on the PPCHex film by inductively coupled plasma-chemical vapor deposition (ICP-CVD).

3. The method according to claim 2, wherein the plasma-polymerized cyclohexane (PPCHex) film is maintained at a substrate temperature of 27° C.

4. The method according to claim 2, wherein the plasma-polymerized cyclohexane (PPCHex) film is deposited using a carrier gas selected from Ar, $N_2$, He and $H_2$.

5. The method according to claim 4, wherein, during step (a), the carrier gas is used at a flow ratio of about 20 sccm.

6. The method according to claim 5, wherein, during step (a), the deposition is conducted under a plasma reaction chamber inner pressure of about 300 mtorr for 30 sec.

7. The method according to claim 4, wherein, during step (a), the deposition is conducted under a plasma reaction chamber inner pressure of about 300 mtorr for 30 sec.

8. The method according to claim 4, wherein, during step (b), the carrier gas is used at a flow ratio of about 15 sccm.

9. The method according to claim 8, wherein, during step (b), the deposition is conducted under a plasma reaction chamber inner pressure of about 30 mtorr for 2 min.

10. The method according to claim 4, wherein, during step (b), the deposition is conducted under a plasma reaction chamber inner pressure of about 30 mtorr for 2 min.

11. The method according to claim 2, wherein, during step (a), ICP power applied from a RF generator of the plasma reaction chamber to an outer electrode is maintained at about 15 W, and SB power applied from the RF generator to a substrate supporter as an inner electrode is maintained at 10 W to 70 W.

12. The method according to claim 2, wherein, during step (b), ICP power applied from a RF generator of the plasma reaction chamber to an outer electrode is maintained at about 4 W, and SB power applied from the RF generator to a substrate supporter as an inner electrode is maintained at about 4 W.

13. A method for manufacturing a protein chip substrate, the method comprising the steps of:
   washing a slide glass with trichloroethylene, acetone and methanol, sequentially;

arranging the slide glass on a substrate supporter inside a plasma reaction chamber;

controlling an inner pressure of the plasma reaction chamber by a vacuum device;

feeding cyclohexane as a precursor together with a carrier gas into the plasma reaction chamber by a bubbler;

controlling an inner temperature of the plasma reaction chamber by a heater under the substrate supporter;

applying inductively coupled plasma (ICP) power and slide voltage (SB) power to an outer electrode and the substrate supporter by the RF generator, respectively, to generate plasma between the slide glass and the plasma reaction chamber;

uniformly depositing a plasma cyclohexane (PPCHex) film on the slide glass while polymerizing cyclohexane as a precursor by plasma; and depositing a plasma-polymerized ethylenediamine (PPEDA) film using ethylenediamine (EDA) as a precursor on the PPCHex film by inductively coupled plasma-chemical vapor deposition (ICP-CVD).

* * * * *